United States Patent [19]

Uemasu et al.

[11] Patent Number: 5,177,302
[45] Date of Patent: Jan. 5, 1993

[54] PROCESS FOR SEPARATING ISOMERS OF DISUBSTITUTED BENZENES AND AGENTS TO BE USED THEREFOR

[75] Inventors: Isamu Uemasu, Tsukuba; Hideki Takahashi, Yokohama, both of Japan

[73] Assignees: Director-General, Agency of Industrial Science and Technology, Tokyo; Ensuiko Sugar Refining Co., Ltd., Yokohama, both of Japan

[21] Appl. No.: 703,885

[22] Filed: May 22, 1991

[30] Foreign Application Priority Data

Nov. 27, 1990 [JP] Japan ............................ 2-320845
Jan. 18, 1991 [JP] Japan ............................ 3-016872
Feb. 5, 1991 [JP] Japan ............................ 3-035178

[51] Int. Cl.⁵ .............. C07C 7/00; C07C 209/00; C07C 17/00
[52] U.S. Cl. .................. 585/864; 585/833; 585/865; 564/424; 570/190; 570/211
[58] Field of Search .............. 585/833, 864, 865; 564/424; 570/190, 211

[56] References Cited

U.S. PATENT DOCUMENTS 3,456,028 7/1969 Gerhold et al. ............... 585/805
5,095,173 3/1992 Uemasu et al. ............... 585/865

FOREIGN PATENT DOCUMENTS

4029489A1 4/1991 Fed. Rep. of Germany.
52-42825 4/1977 Japan.

OTHER PUBLICATIONS

Staerke, vol. 39, No. 10, Oct. 1987, Weinheim De, pp. 357-362; J. Szejtli: "Application of cyclodextrins in the chromatography", p. 358, paragraph 2.1, Germany.
Patent Abstracts of Japan, vol. 12, No. 426 (C-542) (3273) Nov. 10, 1988 of JP-A-63 154 703 (Nikken Kagaku), Jun. 28, 1988, Japan.

*Primary Examiner*—Anthony McFarlane
*Assistant Examiner*—Nhat Phan
*Attorney, Agent, or Firm*—Frishauf, Holtz, Goodman & Woodward

[57] ABSTRACT

This invention is concerned with a process for separating isomers of disubstituted benzenes, wherein a mixture of isomers of disubstituted benzenes is contacted with a substituted cyclodextrin to form inclusion complexes, and desired isomers are recovered therefrom in a highly selective manner. The invention also provides substituted cyclodextrins suited for use in the process. Substituted cyclodextrins used in the process can be recovered and used repeatedly.

16 Claims, No Drawings

PROCESS FOR SEPARATING ISOMERS OF DISUBSTITUTED BENZENES AND AGENTS TO BE USED THEREFOR

BACKGROUND OF THE INVENTION

1. Field of the Invention

The present invention relates to a process for effectively separating isomers of disubstituted benzenes, which are useful as solvents, raw materials for chemical syntheses, etc., and to agents to be used for the separation. More particularly, it relates to a process for separating and recovering isomers of disubstituted benzenes which utilizes substituted cyclodextrins capable of including the isomers in a selective manner in accordance with their size and shape, and to substituted cyclodextrins to be used for the separation.

2. Prior Art

In general, isomers of disubstituted benzenes (i.e., o-, m- and p-isomers) are separated by means of distillation, based on the difference in their boiling points, or by means of crystallization, based on the difference in their melting points. However, since the boiling points of isomers of disubstituted benzenes are distributed within a relatively small range, separation based on distillation requires repeated superfractionation, which is not only time-consuming but requires much energy. On the other hand, separation based on crystallization suffers from the problem of eutectoid, and hence a mixture of the isomers could be separated in an effective manner only when it has a composition which can be substantially free from the problem.

Separation of isomers of disubstituted benzenes can also be effected by means of gas chromatography or high performance liquid chromatography. Although chromatography can be effective for analytical purposes, it is not suited for a commercial scale separation of the isomers. In another known technique, cyclodextrin or chemically modified cyclodextrins are used as an agent for separating isomers of benzene compounds (see, e.g., Japanese Patent Application (Laid Open) No. 42,825/77: "Process for Separating Isomers of Benzene Compounds"). In this process, isomers of benzene compounds are precipitated as inclusion complexes and subjected to a liquid-solid separating operation. However, inclusion complexes of cyclodextrins precipitate in the form of extremely fine precipitates which could be separated only through a highly troublesome solid-liquid separating operation.

It is therefore an object of the invention to provide a process for separating isomers of disubstituted benzenes in a highly selective manner.

It is another object of the invention to provide a process for separating isomers of disubstituted benzenes in an industrially advantageous manner.

It is a further object of the present invention to provide agents to be used for the separation of isomers of disubstituted benzenes.

SUMMARY OF THE INVENTION

There is provided by the present invention a process for separating isomers of disubstituted benzenes (i.e., o-, m- and p-isomers), comprising the steps of:

a) contacting a mixture of isomers of disubstituted benzenes with a substituted cyclodextrin, at least one of which hydrogen atoms contained in the hydroxyl groups is substituted with a substituent selected from the group consisting of glucosyl, maltosyl, maltooligosaccharide residue, methyl, hydroxyethyl, hydroxypropyl, sulfonic acid, alkylenesulfonic acid and carboxyalkyl groups, so as to allow the isomers to form inclusion complexes with said substituted cyclodextrin in accordance with their inclusion complex-forming constants; and b) eliminating the isomers from said inclusion complexes.

The present invention also provides agents to be used for the separation of isomers of disubstituted benzenes, said agents being selected from cyclodextrins, at least one of which hydrogen atoms contained in the hydroxyl groups is substituted with a substituent selected from the group consisting of glucosyl, maltosyl, maltooligosaccharide residue, methyl, hydroxyethyl, hydroxypropyl, sulfonic acid, alkylenesulfonic acid and carboxyalkyl groups.

DETAILED DESCRIPTION OF THE INVENTION

The present invention will further be explained hereinbelow.

In the present invention, substituted cyclodextrins are used as an agent for separating isomers of disubstituted benzenes. Cyclodextrin derivatives to be used in the present invention include α-, β- and γ-cyclodextrins, at least one of the hydrogen atoms of their hydroxyl groups being substituted with a substituent selected from the group consisting of glucosyl, maltosyl, maltooligosaccharide residue, methyl, hydroxyethyl, hydroxypropyl, sulfonic acid, alkylenesulfonic acid and carboxyalkyl groups.

The substituted cyclodextrins per se, as well as inclusion complexes of the substituted cyclodextrins with disubstituted benzenes, are highly soluble in water, in contrast to other cyclodextrins and their inclusion complexes. They can therefore be handled in the form of a concentrated aqueous solution. In addition, no precipitates are generated at the time when inclusion complexes are formed. The use of such substituted cyclodextrins has therefore the advantage that no solid-liquid separation is required and hence the separation process can be simplified.

Formation of inclusion complexes with the substituted cyclodextrins, in particular, glucosyl cyclodextrin and maltosyl cyclodextrin, has been utilized, e.g., in the field of foods. However, no cases have been known wherein the inclusion complex-forming ability of the substituted cyclodextrins is utilized for the separation of isomers of disubstituted benzenes.

In practicing the present invention, one of the substituted cyclodextrins is dissolved into water. To the solution is added a mixture of isomers of disubstituted benzenes, for example, xylenes, dichlorobenzenes, chlorotoluenes, chloronitrobenzenes, nitrotoluenes, dinitrobenzenes, bromotoluenes, chlorobenzotrifluorides, aminothiophenols, divinylbenzenes, vinyltoluenes, aminobenzotrifluorides, bis(trifluoromethyl)benzenes, chlorobenzyl chlorides, fluorobenzyl chlorides, bromonitrobenzenes, fluoronitrobenzenes, difluorobenzenes, fluorotoluenes, fluoroanilines, fluorobenzonitriles, or the like, and then the mixture is vigorously stirred or shaken. The scope of the present invention does not include the case where xylene isomers are separated by using substituted α-cyclodextrins. The substituted cyclodextrins are used at a concentration of 5 to 100% by weight, preferably 10 to 30% by weight, based on the weight of water. If the above procedure is carried out by using a nonsubstituted cyclodextrin or a substituted cyclodextrin other than those according to the invention, there will be resulted an undesirable precipitation of inclusion complexes since their solubility to water is as low as 5% by weight or less. In order to avoid the formation of precipitates, they must be used at an extremely low concentration. On the contrary, the substituted cyclodextrins according to the invention are free from such an inconvenience.

In the above operation, the aqueous solution of substituted cyclodextrin is admixed with the mixture of isomers at such a ratio that the number of disubstituted benzene isomers amounts to 1 to 10 times that of substituted cyclodextrins. The stirring or shaking is conducted as vigorously as possible for a period of from a few seconds to half an hour at a temperature of 10° to 40° C., preferably 20° to 25° C. After the stirring or shaking, the aqueous layer is separated from the oil layer. The separation can be effected by any known methods. For example, the mixture can be subjected to centrifugation for 5 to 10 minutes. If desired, salts can be added to the mixture to improve the efficiency of the separation.

Isomers of disubstituted benzenes included by the substituted cyclodextrins can be eliminated by heating the aqueous layer at a temperature of 60° C. or above, and isomers so eliminated can be separated from the aqueous layer. Alternatively, isomers included by the substituted cyclodextrins can be extracted with a volatile organic solvent which is resistant to inclusion by the substituted cyclodextrins, is hardly soluble to water and has a relatively low boiling point. The extraction is carried out at room temperature or at an elevated temperature of from 60° to 70° C., whereby the aqueous layer is converted into a transparent aqueous solution containing the substituted cyclodextrins. Extracted benzene isomers can be recovered from the organic layer by evaporating the organic solvent.

If the desired isomers could not be separated to a satisfactory degree by a single inclusion, the inclusion operation can be repeated to raise the purity of the desired isomer.

The substituted cyclodextrins according to the invention are not decomposed in any steps of the procedure, and hence the agents can be recovered and used repeatedly.

The substituted cyclodextrins according to the invention can be used for the separation of all the three types of disubstituted benzene isomers (i.e., o-, m- and p-isomers).

The present invention will further be illustrated by examples. In the following examples, all the percentages are based on weight.

EXAMPLE 1

Into 5 g of water was dissolved 0.729 g of monomaltosyl-$\beta$-cyclodextrin. To this solution was added 0.735 g of mixture of o-dichlorobenzene (65%) and p-dichlorobenzene (35%).

The resulting mixture was stirred at 25° C. for 5 minutes and then subjected to centrifugation at 3,000 r.p.m. for 5 minutes. The aqueous layer was separated, and ethyl ether was added to the separated aqueous layer. After thorough shaking, ether layer was separated, and the ether was evaporated off to give an oily product.

The composition of the product was analyzed by capillary gas chromatography. Compositions of the starting mixture and the extracted oily product are shown in Table 1.

TABLE 1

|  | Starting Mixture | Extracted Product |
|---|---|---|
| o-Dichlorobenzene | 65% | 84.2% |
| p-Dichlorobenzene | 35% | 15.8% |

EXAMPLE 2

The procedure of Example 1 was repeated, except that a mixture of o-dichlorobenzene (84%) and p-dichlorobenzene (16%) was used. Results obtained are shown in Table 2.

TABLE 2

|  | Starting Mixture | Extracted Product |
|---|---|---|
| o-Dichlorobenzene | 84% | 93.6% |
| p-Dichlorobenzene | 16% | 6.4% |

EXAMPLE 3

The procedure of Example 1 was repeated, except that a mixture consisting of 93% of o-dichlorobenzene and 7% of p-dichlorobenzene was used. Results obtained are shown in Table 3.

TABLE 3

|  | Starting Mixture | Extracted Product |
|---|---|---|
| o-Dichlorobenzene | 93% | 97.1% |
| p-Dichlorobenzene | 7% | 2.9% |

EXAMPLE 4

The procedure of Example 1 was repeated, except that 0.656 g of methyl-$\beta$-cyclodextrin was used instead of monomaltosyl-$\beta$-cyclodextrin. Results obtained are shown in Table 4.

TABLE 4

|  | Starting Mixture | Extracted Product |
|---|---|---|
| o-Dichlorobenzene | 65% | 77.3% |
| p-Dichlorobenzene | 35% | 22.7% |

EXAMPLE 5

The procedure of Example 1 was repeated, except that 0.722 g of hydroxyethyl-$\beta$-cyclodextrin was used instead of monomaltosyl-$\beta$-cyclodextrin. Results obtained are shown in Table 5.

TABLE 5

|  | Starting Mixture | Extracted Product |
|---|---|---|
| o-Dichlorobenzene | 65% | 74.2% |
| p-Dichlorobenzene | 35% | 25.8% |

EXAMPLE 6

The procedure of Example 1 was repeated, except that a mixture of dichlorobenzenes consisting of an equal quantity of o-, m- and p-isomers was used. Results obtained are shown Table 6

TABLE 6

|  | Starting Mixture | Extracted Product |
|---|---|---|
| o-Dichlorobenzene | 33.3% | 56.2% |
| m-Dichlorobenzene | 33.3% | 25.6% |
| p-Dichlorobenzene | 33.3% | 18.3% |

EXAMPLE 7

Into 10 g of water was dissolved 1.34 g of monogycosyl-$\beta$-cyclodextrin, and 3 g of commercially available xylene (extra pure grade chemical) was added thereto. The resulting mixture was treated in the same manner as in Example 1. Results obtained are shown in Table 7.

TABLE 7

|  | Starting Mixture | Extracted Product |
|---|---|---|
| Ethylbenzene | 17.1% | 11.9% |
| o-Xylene | 20.5% | 43.6% |
| m-Xylene | 43.3% | 26.8% |
| p-Xylene | 18.5% | 17.7% |

EXAMPLE 8

The procedure of Example 7 was repeated, except that 3 g of a mixture consisting of an equal quantity of ethylbenzene, o-xylene, m-xylene and p-xylene was used instead of the commercially available xylene. Results obtained are shown in Table 8.

TABLE 8

|  | Starting Mixture | Extracted Product |
|---|---|---|
| Ethylbenzene | 25.0% | 15.8% |
| o-Xylene | 25.0% | 49.5% |
| m-Xylene | 25.0% | 15.4% |
| p-Xylene | 25.0% | 19.3% |

EXAMPLE 9

The procedure of Example 7 was repeated, except that a mixture of xylenes consisting of an equal quantity of m- and p-isomers was used instead of the commercially available xylene. Results obtained are shown in Table 9.

TABLE 9

|  | Starting Mixture | Extracted Product |
|---|---|---|
| m-Xylene | 50.0% | 37.0% |
| p-Xylene | 50.0% | 63.0% |

EXAMPLE 10

Into 5 g of water was dissolved 0.729 g of monomaltosyl-$\beta$-cyclodextrin, and a mixture consisting of 63% of o-nitrotoluene, 4% of m-nitrotoluene and 33% of p-nitrotoluene was added thereto. The resulting mixture was treatment in the same manner as in Example 1. Results obtained are shown Table 10

TABLE 10

|  | Starting Mixture | Extracted Product |
|---|---|---|
| o-Nitrotoluene | 63.0% | 74.5% |
| m-Nitrotoluene | 4.0% | 2.4% |
| p-Nitrotoluene | 33.0% | 23.1% |

EXAMPLE 11

Into 5 g of water was dissolved 0.729 g of monomaltosyl-$\beta$-cyclodextrin, and 0.905 g of a mixture of chlorobenzotrifluorides (CBTF) consisting of an equal quantity of o-, m- and p-isomers was added thereto. The resulting mixture was treated in the same manner as in Example 1. Results obtained are shown in Table 11.

TABLE 11

|  | Starting Mixture | Extracted Product |
|---|---|---|
| o-CBTF | 33.3% | 42.2% |
| m-CBTF | 33.3% | 45.9% |
| p-CBTF | 33.3% | 11.9% |

EXAMPLE 12

Into 5 g of water was dissolved 0.729 g of monomaltosyl-$\beta$-cyclodextrin, and 0.906 g of a mixture of chlorobenzotrifluorides (CBTF) consisting of an equal quantity of o- and p-isomers was added thereto. The resulting mixture was treated in the same manner as in Example 1. Results obtained are shown in Table 12.

TABLE 12

|  | Starting Mixture | Extracted Product |
|---|---|---|
| o-CBTF | 50.0% | 71.4% |
| p-CBTF | 50.0% | 28.6% |

EXAMPLE 13

Into 5 g of water was dissolved 0.584 g monoglucosyl-$\alpha$-cyclodextrin, and 0.70 g of a mixture of nitrotoluenes consisting of an equal quantity of o-, m- and p-isomers was added thereto. The resulting mixture was treated in the same manner as in Example 1. Results obtained are shown in Table 13.

TABLE 13

|  | Starting Mixture | Extracted Product |
|---|---|---|
| o-Nitrotoluene | 33.3% | 6.8% |
| m-Nitrotoluene | 33.3% | 22.2% |
| p-Nitrotoluene | 33.3% | 71.0% |

EXAMPLE 14

Into 5 g of water was dissolved 0.568 g of monoglycosyl-$\alpha$-cyclodextrin, and 0.74 g of a mixture of dichlorobenzenes consisting of 65% of o-isomer and 35% of p-isomer was added thereto. The resulting mixture was treated in the same manner as in Example 1. Results obtained are shown in Table 14.

TABLE 14

|  | Starting Mixture | Extracted Product |
|---|---|---|
| o-Dichlorobenzene | 65.0% | 31.0% |
| p-Dichlorobenzene | 35.0% | 69.0% |

What is claimed is:

1. A process for separating o, m- or p-isomers of a disubstituted benzene, comprising the steps of:
   (a) contacting a mixture of isomers of a disubstituted benzene with a substituted cyclodextrin, said disubstituted benzene selected from the group consisting of xylenes, dichlorobenzenes, chlorotoluenes, chloronitrobenzenes, nitrotoluenes, dinitrobenzenes, bromotoluenes, chlorobenzotrifluorides, aminothiophenols, divinylbenzenes, vinyltoluenes, aminobenzotrifluorides, bis(trifluoromethyl)benzenes, chlorobenzyl chlorides, flurorobenzyl chlorides, bromonitrobenzenes, fluoronitrobenzenes, difluorobenzenes, fluorotoluenes, fluoroanilines and fluorobenzonitriles, at least one of the hydrogen atoms contained in the hydroxyl groups of said cyclodextrin is substituted with a substituent selected from the group consisting of glucosyl, maltosyl, maltooligosaccharide residue, methyl, hydroxyethyl, hydroxypropyl, sulfonic acid, alkylenesulfonic acid and carboxyalkyl groups, so as to allow the isomers to form inclusion complexes with said substituted cyclodextrin in accordance with their inclusion complex-forming constants; and (b) extracting the isomers from said inclusion complexes, excluding the separation of xylene isomers with a substituted α-cyclodextrin.

2. The process according to claim 1, wherein the substituted cyclodextrin is dissolved in water.

3. The process according to claim 2, wherein the substituted cyclodextrin is in a concentration of 5 to 100% by weight, based on the weight of the water.

4. The process according to claim 2, wherein the substituted cyclodextrin is in a concentration of 10 to 30% by weight, based on the weight of the water.

5. The process according to claim 4, wherein the aqueous solution of the substitute cyclodextrin is admixed with the mixture of isomers in a ratio such that the number of disubstituted benzene isomers is 1 to 10 times that of the substituted cyclodextrin.

6. The process according to claim 5, wherein the contacting of the mixture of isomers and the substituted cyclodextrin is carried out by stirring or shaking at a temperature of 10° to 40° C. and thereafter an aqueous layer is separated from an oil layer.

7. The process according to claim 6, wherein the separating of the isomers from said inclusion complexes is carried out at a temperature of 60° to 70° C.

8. The process according to claim 7, wherein the substituted cyclodextrin is selected from the group consisting of monomaltosyl-β-cyclodextrin, methyl-β-cyclodextrin, hydroxyethyl-β-cyclodextrin, monogycosyl-β-cyclodextrin and monoglucosyl-α-cyclodextrin.

9. The process according to claim 8, wherein the isomers of disubstituted benzene are o-dichlorobenzene and p-dichlorobenzene.

10. The process according to claim 8, wherein the isomers of the disubstituted benzene are o-dichlorobenzene, p-dichlorobenzene and m-dichlorobenzene.

11. The process according to claim 8, wherein the isomers of the disubstituted benzene are o-xylene, m-xylene and p-xylene.

12. The process according to claim 8, wherein the isomers of the disubstituted benzene are m-xylene and p-xylene.

13. The process according to claim 8, wherein the isomers of the disubstituted benezenes are o-nitrotoluene, m-nitrotoluene and p-nitrotoluene.

14. The process according to claim 8, wherein the isomers of the disubstituted benzene are o-chlorobenzotrifluoride, m-chlorobenzotrifluoride and p-chlorobenzotrifluoride.

15. The process according to claim 8, wherein the isomers are o-chlorobenzotrifluroride and p-chlorobenzotrifluoride.

16. The process according to claim 8, wherein the isomers are o-chlorotoluene and p-chlorotoluene.

* * * * *